United States Patent
Brown et al.

(10) Patent No.: US 6,330,426 B2
(45) Date of Patent: *Dec. 11, 2001

(54) SYSTEM AND METHOD FOR REMOTE EDUCATION USING A MEMORY CARD

(76) Inventors: Stephen J. Brown, 1525 Nadina St., San Mateo, CA (US) 94402; Roger Quy, 1550 Tiburon Blvd., Suite A, Belvedere, CA (US) 94920

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/119,546

(22) Filed: Jul. 20, 1998

Related U.S. Application Data (63) Continuation-in-part of application No. 08/953,883, filed on Oct. 20, 1997, now abandoned, which is a continuation-in-part of application No. 08/757,129, filed on Dec. 3, 1996, now Pat. No. 6,144,837, which is a continuation-in-part of application No. 08/334,643, filed on Nov. 4, 1994, now Pat. No. 5,601,435, which is a continuation-in-part of application No. 08/857,187, filed on May 15, 1997, now Pat. No. 5,918,603, which is a continuation-in-part of application No. 08/247,716, filed on May 23, 1994, now Pat. No. 5,678,571.

(51) Int. Cl.$^7$ .................................................... G09B 5/00

(52) U.S. Cl. ..................... 434/307 R; 434/118; 434/350; 434/362; 128/897

(58) Field of Search .................................... 434/118, 236, 434/237, 267, 258, 262, 265, 307 R, 308, 320, 322, 323, 350, 353, 362, 365; 128/897, 904, 905, 924; 600/300; 345/302, 377, 329, 336, 501; 702/22, 84, 85; 701/1, 300; 340/438, 439, 988; 380/21, 273; 436/43, 48

(56) References Cited

U.S. PATENT DOCUMENTS 4,130,881   12/1978   Haessler et al. .
4,347,851    9/1982   Jundanian .

(List continued on next page.)

FOREIGN PATENT DOCUMENTS

WO 93/02622   2/1993   (WO) .
WO 94/16774   8/1994   (WO) .

OTHER PUBLICATIONS

Brochure of "Introducing the Next Generation of About Your Diabetes", U.S. Pharmacopeial Convention and American Diabetes Association, 1993.

*Primary Examiner*—Joe H. Cheng
(74) *Attorney, Agent, or Firm*—Black Lowe & Graham PLLC (57) ABSTRACT

The present invention is a system and method for allowing an individual to view a program remotely. In the preferred embodiment, the invention is used as a healthcare education system. The system comprises a file server which is coupled to a database storing the educational programs. A remote interface coupled to the file server allows an administrator to assign educational programs to an individual. The remote interface also includes a memory card writer which records the individual identification code and the address of the file server on this memory card. Then, the individual may take the memory card with them. When the individual places the memory card in the memory card reader of a multimedia processor, the processor uses the file server address to automatically connect to the file server. The file server receives the individual identification code from the processor, retrieves the corresponding educational program from the database, and sends the program to the processor to be displayed. After the individual has watched the educational program, completion data in the form of the date and time the program was watched and/or the individual's response, is sent from the multimedia processor to the file server. The completion data can then be viewed by the administrator on a report screen.

24 Claims, 7 Drawing Sheets

U.S. PATENT DOCUMENTS

| | | |
|---|---|---|
| 4,360,345 | 11/1982 | Hon . |
| 4,576,578 | 3/1986 | Parker et al. . |
| 4,729,381 | 3/1988 | Harada et al. . |
| 4,779,199 | 10/1988 | Yoneda et al. . |
| 4,796,639 | 1/1989 | Snow et al. . |
| 4,803,625 | 2/1989 | Fu et al. . |
| 4,907,973 | 3/1990 | Hon . |
| 4,933,873 | 6/1990 | Kaufman et al. . |
| 5,024,225 | 6/1991 | Fang . |
| 5,025,374 | 6/1991 | Roizen et al. . |
| 5,056,059 | 10/1991 | Tivig et al. . |
| 5,111,817 | 5/1992 | Clark et al. . |
| 5,120,230 | 6/1992 | Clark et al. . |
| 5,222,020 | 6/1993 | Takeda . |
| 5,307,263 | 4/1994 | Brown . |
| 5,366,896 * | 11/1994 | Margrey et al. ........................ 436/48 |
| 5,454,722 | 10/1995 | Holland et al. . |
| 5,456,606 | 10/1995 | McIntyre . |
| 5,597,307 | 1/1997 | Redford et al. . |
| 5,624,265 | 4/1997 | Redford et al. . |
| 5,631,844 * | 5/1997 | Margrey et al. ........................ 702/22 |
| 5,678,562 | 10/1997 | Sellers . |
| 5,760,771 | 6/1998 | Blonder et al. . |
| 5,810,747 | 9/1998 | Brudny et al. . |
| 5,825,283 | 10/1998 | Camhi . |
| 5,879,163 | 3/1999 | Brown et al. . |
| 5,897,493 | 4/1999 | Brown . |
| 5,913,310 * | 6/1999 | Brown ................................ 128/897 |
| 5,933,136 | 8/1999 | Brown . |
| 6,055,314 * | 4/2000 | Spies et al. ........................... 380/21 |
| 6,055,487 * | 4/2000 | Margery et al. ........................ 702/84 |

* cited by examiner

PROGRAM ASSIGNMENT SCREEN

AVAILABLE PROGRAMS:   STUDENTS:

- [X] DIABETES AND EXERCISE
- [ ] FOOD EXCHANGES AND DIET
- [ ] BLOOD GLUCOSE MONITORING

- [X] DAN LINDSEY
- [ ] MARK SMITH
- [ ] DEAN JONES

[ADD NEW PROGRAM] [SAVE NEW LISTING] [ADD NEW PATIENT]

[ASSIGN PROGRAM] [DELETE PROGRAM]

FIG. 3

REPORT SCREEN

| STUDENT | ASSIGNED PROGRAM | PROGRAM COMPLETED | RESULTS/SCORE |
|---|---|---|---|
| DAN LINDSEY | DIABETES AND EXERCISE | MAY 1, 1997 5:22 PM | COMPLETED |
| MARK SMITH | FOOD EXCHANGES AND DIET | MAY 3, 1997 3:54 PM | 79 |
| DEAN JONES | BLOOD GLUCOSE MONITORING | NOT COMPLETED | N/A |

FIG. 4

Thank you for watching "Living With Diabetes", brought to you by Acme Pharmaceuticals. Please answer the following questions by pushing the numbered button on your remote control which corresponds to the best answer.

A. Do you visit your doctor regularly?
    1 - yes    2 - sometimes    3 - no B. Do you monitor your sugar (glucose) intake?
    1 - yes    2 - sometimes    3 - no C. Do you exercise regularly?
    1 - yes    2 - sometimes    3 - no

SYSTEM AND METHOD FOR REMOTE EDUCATION USING A MEMORY CARD

RELATED APPLICATIONS

This application is a continuation-in-part of the application Ser. No. 08/953,883 filed on Oct. 20, 1997, now abandoned which in turn is a continuation-in-part of application Ser. No. 08/757,129 filed on Dec. 3, 1996, which is now U.S. Pat. No. 6,144,837 issued on Nov. 7, 2000, which in turn is a continuation-in-part of patent application Ser. No. 08/334,643 filed on Nov. 4, 1994, which is now U.S. Pat. No. 5,601,435 issued on Feb. 11, 1997.

This application is also a continuation of application Ser. No. 08/958,786, which is now U.S. Pat. No. 5,913,310, issued on Jun. 22, 1999, which is a continuation-in-part of application Ser. No. 08/857,187, filed May 15, 1997, now U.S. Pat. No. 5,918,603 which is a continuation of application Ser. No. 08/247,716, filed May 23, 1994, now U.S. Pat. No. 5,678,571, issued on Oct. 21, 1997.

All of the above applications are herein incorporated by reference.

FIELD OF THE INVENTION

The present invention generally relates to remote education systems. More particularly, this present invention relates to a system and method of remote health education in which an individual is provided with a memory card capable of being placed in a multimedia processor to automatically access selected educational health programs.

BACKGROUND OF THE INVENTION

One of the biggest problems many healthcare providers face is their patients' lack of knowledge. Patients may lack knowledge on basic preventative measures, such as why they should exercise, eat right, and not smoke. Patients may also lack knowledge on conditions or diseases they do have, such as how to measure their blood glucose levels if they are diabetic. This lack of knowledge is a problem for healthcare providers because patients who do not know how to take care of themselves are ill more frequently. Thus, they tend to visit their doctors more often and also tend to incur additional costs for hospital stays or laboratory tests. This results in greater fees for the patient, his or her insurance company, and often the taxpayers.

An example of this problem is seen in some diabetes patients. Diabetic patients must regularly receive insulin shots and adhere to a specific diet in order to control their blood glucose levels. Unfortunately, some diabetic patients do not understand all the reasons why they should have regular insulin shots or why they should or should not eat certain foods. In addition, many diabetic patients are unaware of the health consequences should they deviate from their treatment plan. As a result, uninformed patients usually become sicker and require more medical treatment when compared to patients who understand all aspects of their diseases. Sicker patients require more healthcare, which is expensive and time-consuming for healthcare professionals, insurance companies, and the patients themselves.

One way to solve this problem is to increase the amount of education patients receive about their lifestyle choices and/or their diseases. When patients know what is required to stay healthy, they are less likely to become ill and require treatment. In addition, if patients understand the health problems that will result from not taking care of themselves, they will be more likely to follow their prescribed treatments.

Presently, forms of health education range from pamphlets in a doctor's office to radio announcements and television shows. Paper-based educational materials such as pamphlets are cheap and easy to both produce and distribute. Unfortunately, pamphlets or articles are limited to words and pictures and are usually quite boring, which makes it less likely that patients read them. Radio announcements and television shows are more lively and entertaining, but they indiscriminately broadcast to the general public. Accordingly, these radio announcements and television show cannot be customized to a particular patient.

Due to technological advances, patients can now be educated using CD-ROMs, the Internet, and multimedia processors. U.S. Pat. No. 5,307,263 by the present inventor discloses a modular, microprocessor-based health monitoring system. The hand-held unit has a display screen, a control button pad, interchangeable program cartridges, and sensors for monitoring a variety of healthcare data. The program cartridges include motivational and educational material related to use of the device, including step-by-step instructions. Acquired data may be transmitted to a data management unit via an interface cable, or to a clearing house via telephone lines. A program cartridge for monitoring glucose levels and a glucose sensor is disclosed for the purpose of caring for children with diabetes.

U.S. Pat. Nos. 5,597,307 and 5,624,265 by Redford and Stern describe an educational system and apparatus aimed at children which also uses a multimedia processor. This invention comprises a remote control located in a book or other printed publication. A child reads the book while watching the display generated by the multimedia processor, and then press the buttons in the remote control book to alter what he sees.

None of these prior art education systems allow an individual to automatically access assigned educational programs remotely. These inventions described above provide general educational programs which are not tailored to the specific needs of an individual. These systems do not allow a healthcare provider or teacher to easily custom-design an educational program to be viewed by the individual. Further, none of these systems provide confirmation that the individual completed the educational program. Finally, none of these systems provide a patient or individual access to an unlimited number of educational programs.

SUMMARY OF THE INVENTION

The present invention comprises a system and method for remote education using a memory card. This system preferably comprises a database, a file server, a remote interface, a memory card writer, a display unit, a multimedia processor, and a card reader. The file server acts as a central hub of the system, because it is preferably coupled to the database, the remote interface, and the multimedia processor. Accordingly, these three components are capable of being located a long distance from one another. The database preferably stores a plurality of educational programs. Preferably, the remote interface allows an administrator, such as a healthcare provider or educator, to assign a particular educational program to an individual. The identification code of the individual and a pointer referring to the assigned educational program are preferably stored on memory means of the file server. Preferably, by using the memory card writer, the administrator is capable of recording the individual's identification code and the address of the file server onto the memory card.

After the administrator assigns the particular educational program to the individual, the memory card can be given to the individual. When the individual wishes to view the assigned educational program, the individual simply places the card in the card reader. Preferably, the memory card reader is coupled to or located within the multimedia processor, which in turn is coupled to the file server. Upon receiving the memory card, the multimedia processor preferably sends the individual's identification code to the file server. Preferably, the file server then calls up the assigned educational program from the database. The content of the educational program is sent to the multimedia processor and displayed on a display unit for the individual.

Preferably, the file server is notified when the individual has completed the educational program. Completion data includes the date and time the individual watched the educational program. Further, the completion data can also include responses made by the individual to the educational program. Preferably, the file server records the completion data and then sends the completion data to the remote interface for the administrator to review.

In the preferred embodiment of the remote education system, the file server is a web server, the remote interface is an interactive web page, and the communication link is the Internet. An administrator preferably assigns an educational program to the individual by entering the assignment information onto the web page. Preferably, the assignment information is sent to the web server. When the individual places the memory card into the card reader, the multimedia processor preferably sends the individual's identification code to the web server, which in turn, preferably calls up the educational program from the database. In the preferred embodiment, the database comprises one or more web servers, which allows the administrator to assign to the individual an unlimited amount of material.

In the preferred embodiment, the memory card is a plastic card with a magnetic information strip, similar to an ordinary credit card. The magnetic strip preferably contains the individual's identification code and the location of the file server. In another embodiment, the memory card comprises a circuit. The circuit preferably contains the individual's identification code and the location of the file server.

It is an object of the present invention to provide an individual with a remote education system which can be accessed from the individual's home. It is another object of the invention to provide a remote education system which displays educational programs for an individual. It is another object of the present invention to provide interactive educational programs. Another object of the invention is to provide a remote education system comprising a memory card containing an individual's identification code and the locations of educational programs for the individual to view. It is another object of the present invention to provide confirmation that an individual has completed an educational program. It is another object of the invention to provide a remote education system through a network or computers such as the Internet. Yet another object of the present invention is to provide a remote healthcare education system for patients. It is another object of the present invention to allow a healthcare provider to assign educational programs for a patient by using a memory card.

These and other objects and advantages will become more apparent after consideration of the following description and the accompanying drawings.

DETAILED DESCRIPTION

The present invention provides a system and method for remotely educating an individual using a memory card. In the preferred embodiment, the present invention is used to distribute custom-designed health education programs to patients. However, it is to be understood that the invention is not limited to the healthcare industry. The system and method of the invention may be used for any type of remote education application in any field.

Figure 1:
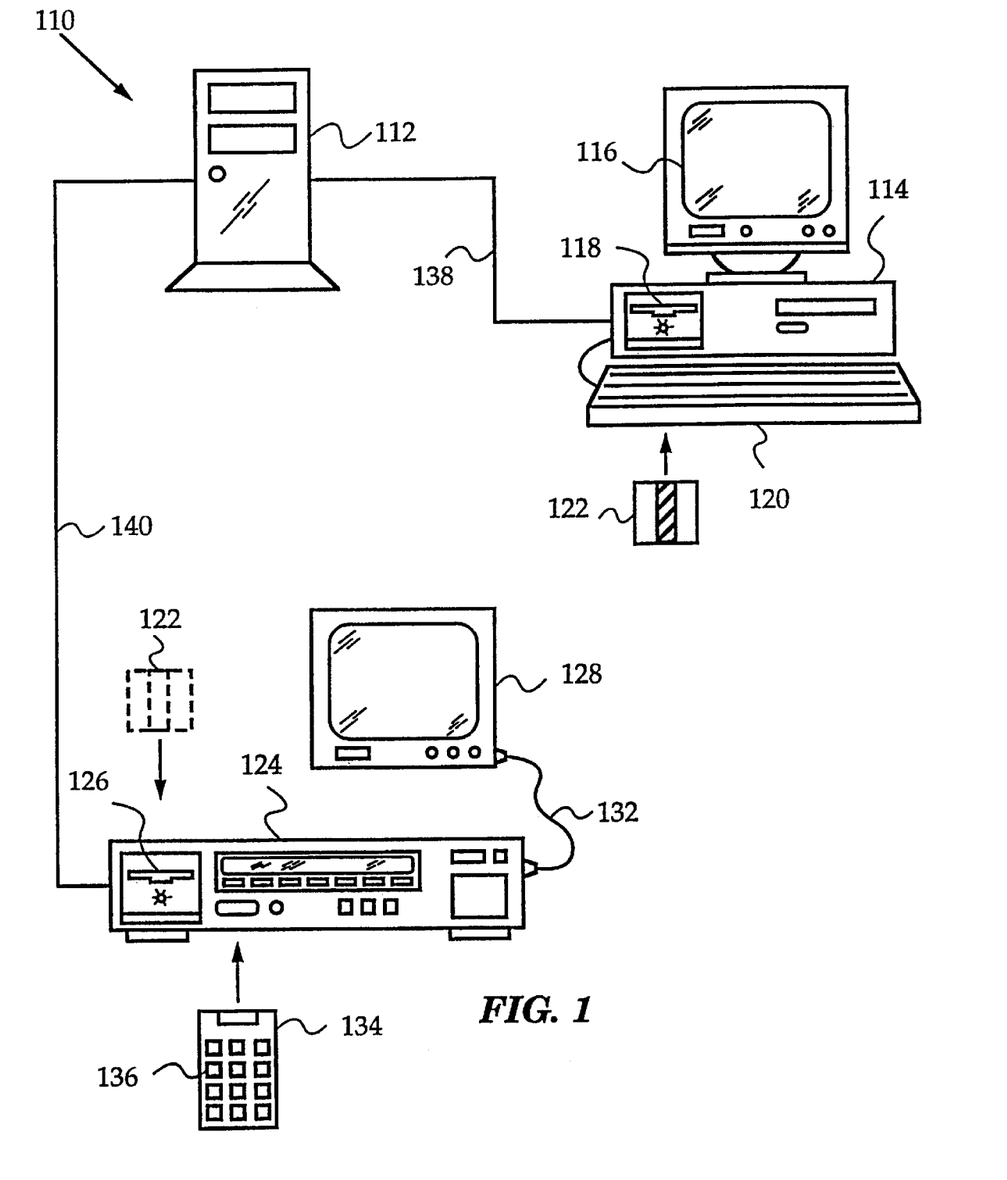
FIG. 1 is a schematic diagram of the remote education system according to the preferred embodiment of the present invention.

The preferred embodiment of the system is shown in FIG. 1. The system 110 comprises a file server 112, which is coupled by communication links 138, 130, and 140 to a remote interface 114, a database 148 preferably containing educational programs, and a multimedia processor 124. The file server 112 is preferably a world wide web server, the remote interface 114 is preferably a web page, and the communication links 138 and 130 are preferably the Internet. The remote interface 114 preferably includes a display 116 and a keyboard 120, which an administrator preferably utilizes to assign an educational program to an individual. The remote interface 114 is also preferably coupled to a memory card writer 118. Preferably, the memory card writer 118 records the individual's identification code and the location of the file server 112 on a memory card 122. Preferably, the location of file server 112 is in the form of a uniform resource locator, or URL.

The communication link 140 from the file server 112 to the multimedia processor 124 is preferably the Internet. However, the file server 112 and the multimedia processor 124 are also capable of contacting each other via wireless communication networks, cellular networks, telephone networks, or any other suitable network. The multimedia processor 124 is also preferably connected by a communication link 132 to a display 128, which is used to display educational programs to the individual. Preferably, the communication link 132 is any suitable connection means. Preferably, the display 128 is a standard audiovisual display, such as a television.

The multimedia processor 124 is preferably coupled to a memory card reader 126. When the memory card 122 is placed in the memory card reader 126, the assignment information is sent to the file server 112. Preferably, the file server 112 then retrieves the assigned educational program from the database 148. The assigned educational program is then preferably sent through communication link 140 to the multimedia processor 124 and preferably shown on the display 128. In addition, the multimedia processor 124 also preferably comprises expansion ports to support additional user interfaces and devices, such as keyboards and trackballs, as well as add-on circuits for enhanced sound, video, or processing performance (not shown).

As shown in FIG. 1, input device 134 comprises numerous momentary contact push buttons 136 which are preferably used by the individual to control and respond to the assigned educational program. These push buttons 136 preferably represent control functions, such as "on" and "off", as well as numbers, letters, or various commands, such as "yes" and "no". Alternatively, these push buttons 136 may be replaced by switches, keys, a touch sensitive display screen, or any other data input device. The input device 134 is preferably a standard wireless communication means which sends command signals to the multimedia processor 124 for processing and execution. However, any communication means may be utilized which allows the input device 134 to communicate with the multimedia processor 124.

For clarity of illustration, only one database and only one multimedia processor are shown in FIG. 1. It is to be understood that system 110 may include any number of databases for storing any number of educational programs, and any number of multimedia processors for use by any number of individuals.

Figure 2:
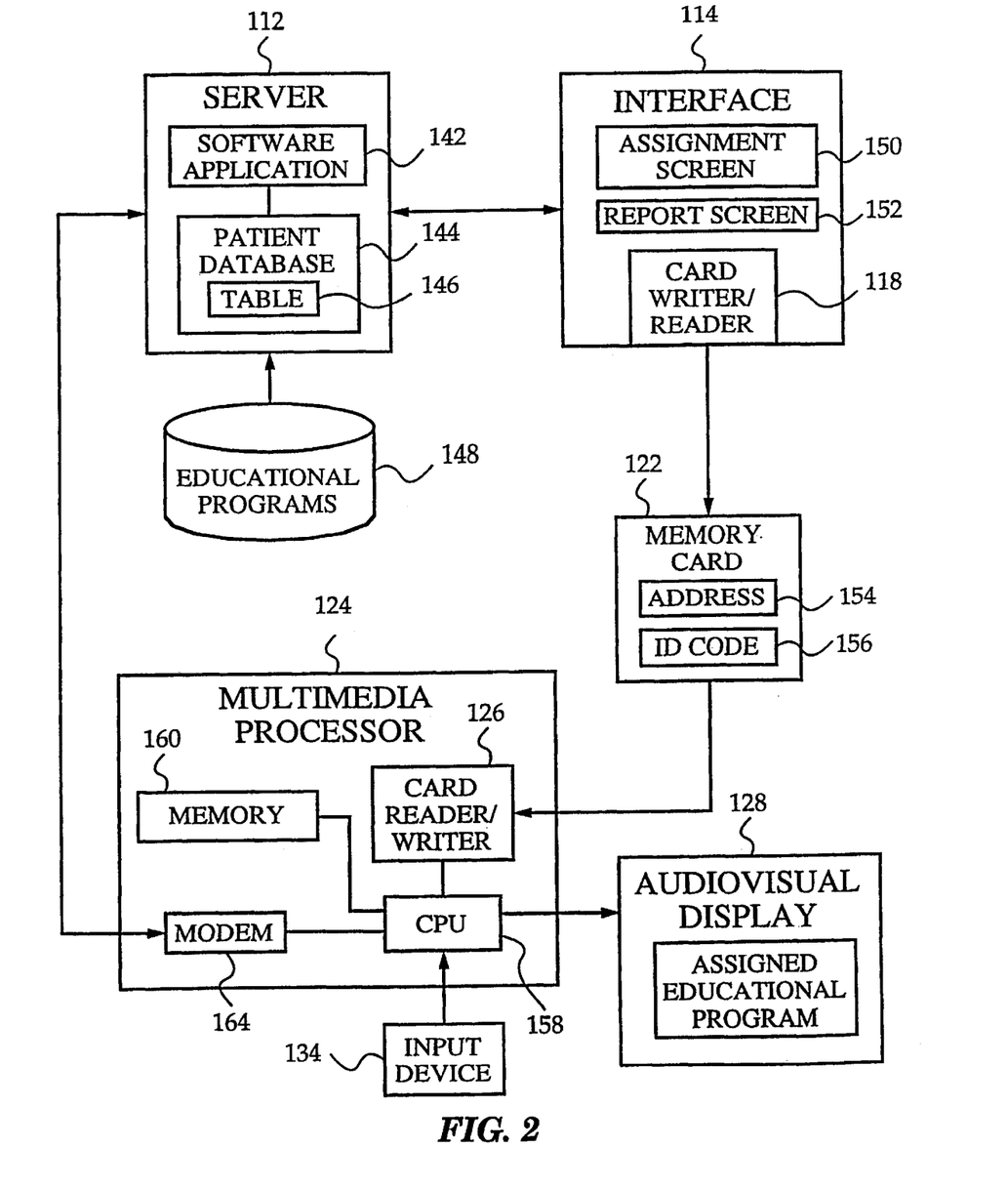
FIG. 2 is a block diagram showing the components of the preferred embodiment, according to FIG. 1.

FIG. 2 shows a detailed block diagram of the preferred embodiment of the present invention as illustrated in FIG. 1. The server 112 preferably includes a general software application 142 which is used create a patient database 144 and a patient table 146. Preferably, the software application 142 is also capable of programming the file server 112 to carry out standard commands such as receiving, saving, and transmitting information. The patient database 144 is preferably coupled to the database 148 containing the educational programs. Alternatively, the patient database 144 can also contain pointers to the database 148 containing the educational programs. The advantage of utilizing the pointers is that they allow the healthcare provider to assign any number of the educational programs within the database 148 to the individual, as long as the educational programs within the database 148 are capable of being transmitted to the multimedia processor 124 and shown on the display 28. Thus, suitable forms of educational programs within the database 148 preferably include photos, videos, animation, static web pages, interactive web pages, etc. Preferably, the patient table 146, which is stored in the memory of the file server 112, lists the patients, their identification codes, and educational programs within the database 148 which have been assigned to them.

Figure 3:
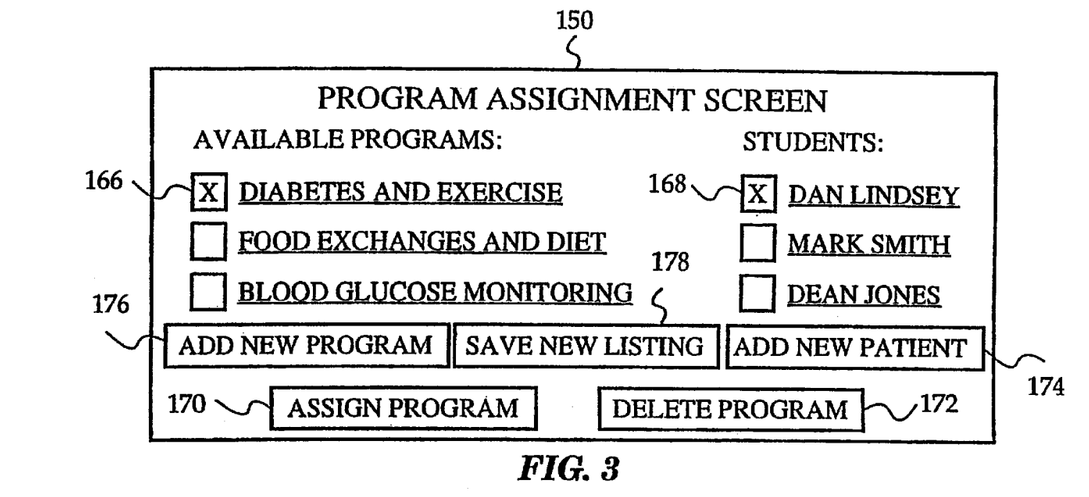
FIG. 3 is a sample program assignment screen of the preferred embodiment.

Preferably, the patient table 146 is generated by information entered into an assignment screen 150 of the remote interface 114. This assignment screen 150, which is illustrated in FIG. 3, preferably lists available educational programs within the database 148, each with a corresponding check box 166, and patients, also each with a corresponding check box 168. The administrator preferably brings up the assignment screen 150 on the display 116 of the remote interface 114. The administrator preferably selects a check box 168 for a patient and then preferably selects a check box 166 corresponding to educational program within the database 148 to be assigned to the patient. More than one educational program within the database 148 may be assigned to each patient. In addition, more than one patient may be assigned the same educational program within the database 148. The administrator then preferably selects an ASSIGN PROGRAM button 170, which preferably stores the assignment in the patient table 146. The assignment screen 150 also preferably includes a DELETE PROGRAM button 172, which allows the administrator to erase the assignment.

Preferably, new listings of patients and educational programs within the database 148 are easily created by the administrator by clicking on an ADD NEW PATIENT button 174 or an ADD NEW PROGRAM button 176, respectively. Preferably, when the ADD NEW PATIENT button 174 button is selected, a new field is added to the patient category, and the administrator then types in a name of a new patient. Likewise, when the ADD NEW PROGRAM button 176 is selected, a new field is preferably added to the program category, and the administrator then preferably types in a name of the new educational program within the database 148. Preferably, after pressing either the ADD NEW PATIENT button 174 or the ADD NEW PROGRAM button 176, the administrator finally saves the addition by clicking on a SAVE NEW LISTING button 178. The new listings are preferably then saved in the patient table 146.

In the preferred embodiment, the remote interface 114 is a web page. Thus, using the keyboard 120, as shown in FIG. 1, the administrator preferably creates customized educational programs in the form of static or interactive web pages for patients. The administrator creates the web page using a scripting language such as HTML or Java, and then stores it on the patient database 144. These web pages can be accessed by the multimedia processor 124 in the same manner as the above mentioned educational programs within the database 148.

Figure 4:
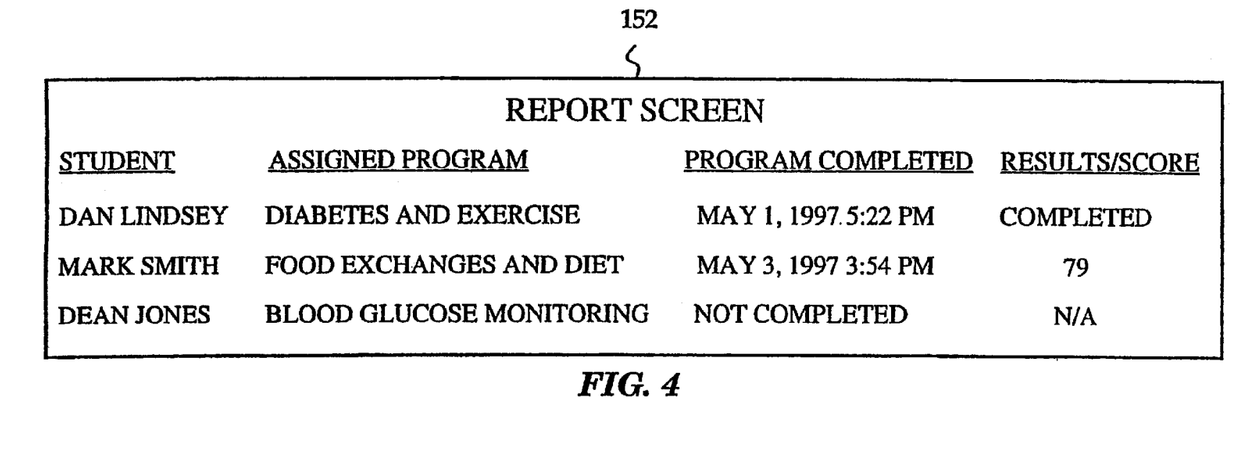
FIG. 4 is a sample report screen of the preferred embodiment.

Referring to FIG. 2 again, the remote interface 114 also preferably comprises a report screen 152 which is preferably shown on display 116. The report screen 152, as illustrated in FIG. 4, preferably informs the administrator when the patient has completed watching the assigned educational program within the database 148 and/or a program score. Specific techniques for writing report generator programs to display data in this manner are well known in the art.

Figure 5:
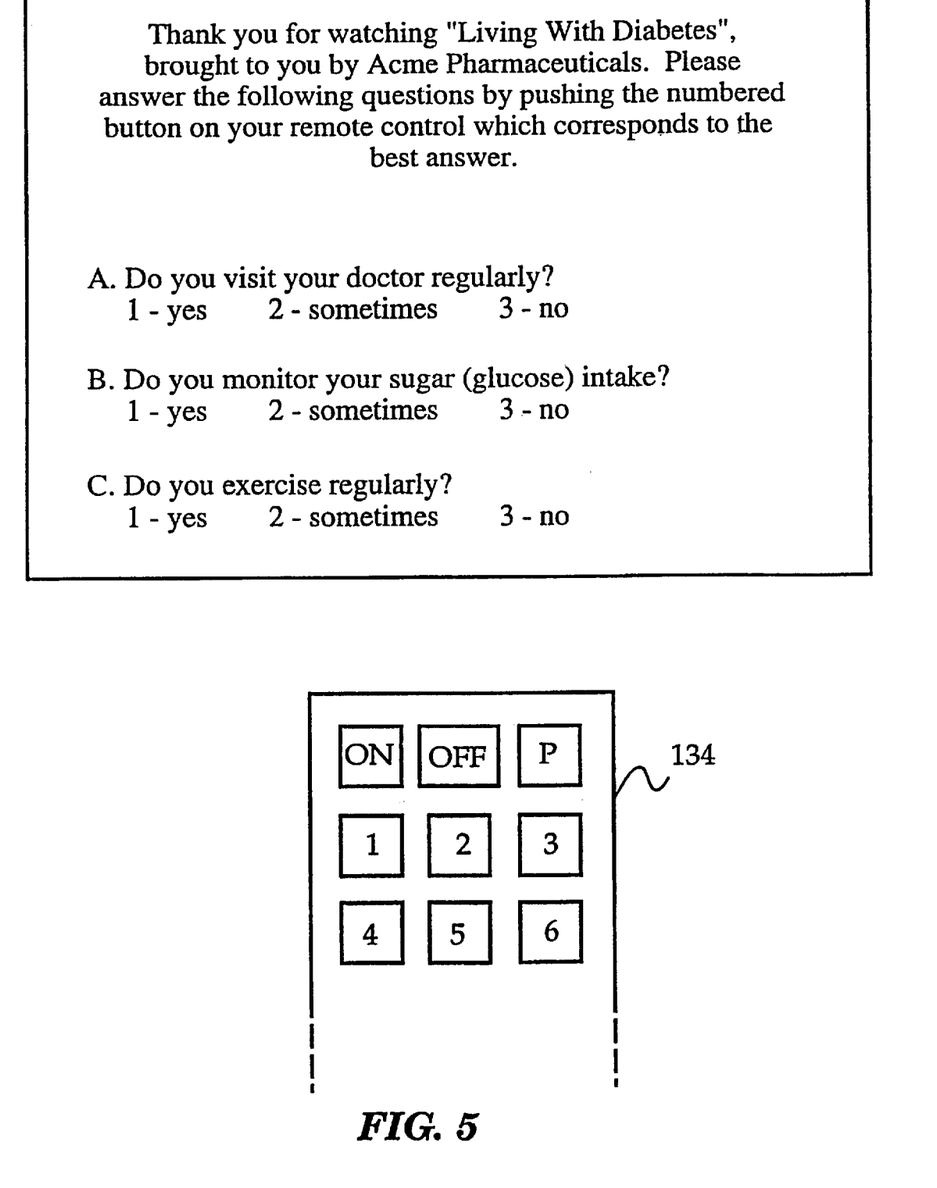
FIG. 5 is a sample interactive educational program of the preferred embodiment.

The program score is generally determined by evaluating patient responses to an interactive educational program, such as an interactive web page. FIG. 5 shows a sample educational program which includes questions for the patient to answer preferably using the input device 134.

The memory card writer 118 is preferably coupled to the remote interface 114. The memory card writer 118 preferably encodes information onto a magnetic strip or circuit. The process of storing information on a magnetic strip or circuit is well known in the art. The memory card 122 preferably contains a patient identification code 156 and a file server address 154.

As shown in FIG. 2, the multimedia processor 124 also preferably comprises a memory means 160, a memory card reader 126 a central processing unit (CPU) 158, a modem 164, and an audiovisual display 128. The memory card reader 126, memory means 160, modem 164, and audiovisual display 128 are all preferably coupled to the CPU 158. Preferably, the multimedia processor 124 couples to the file server 112 via the modem 164 and the communication link 40, which is preferably a telephone cable. Preferably, the multimedia processor 124 is programmed to automatically dial out using the modem 164 whenever the memory card 122 is placed in the memory card reader 126.

Preferably, the memory card reader 126 comprises means for detecting and interpreting the information stored on the memory card 122. In the preferred embodiment, the memory card reader 126 is a magnetic strip reader. When the patient places the memory card 122 into the memory card reader 126, the information is preferably sent to the CPU 158 and then to the memory means 160. Preferably, the information is then sent to the file server 112 via the modem 164.

The memory means 160 of the multimedia processor 124 preferably stores program instructions on how to connect to the file server 112 and how to transmit the patient identification code 156. In addition, the memory means 160 preferably receives and stores the assigned educational programs within the database 148 from the file server 112. When the content of these educational programs within the database 148 is sent to the multimedia processor 124 from the file server 112, the memory means 160 preferably translates the content of the educational programs within the database 148 into audiovisual signals to be shown on the display 128.

Figure 6A:
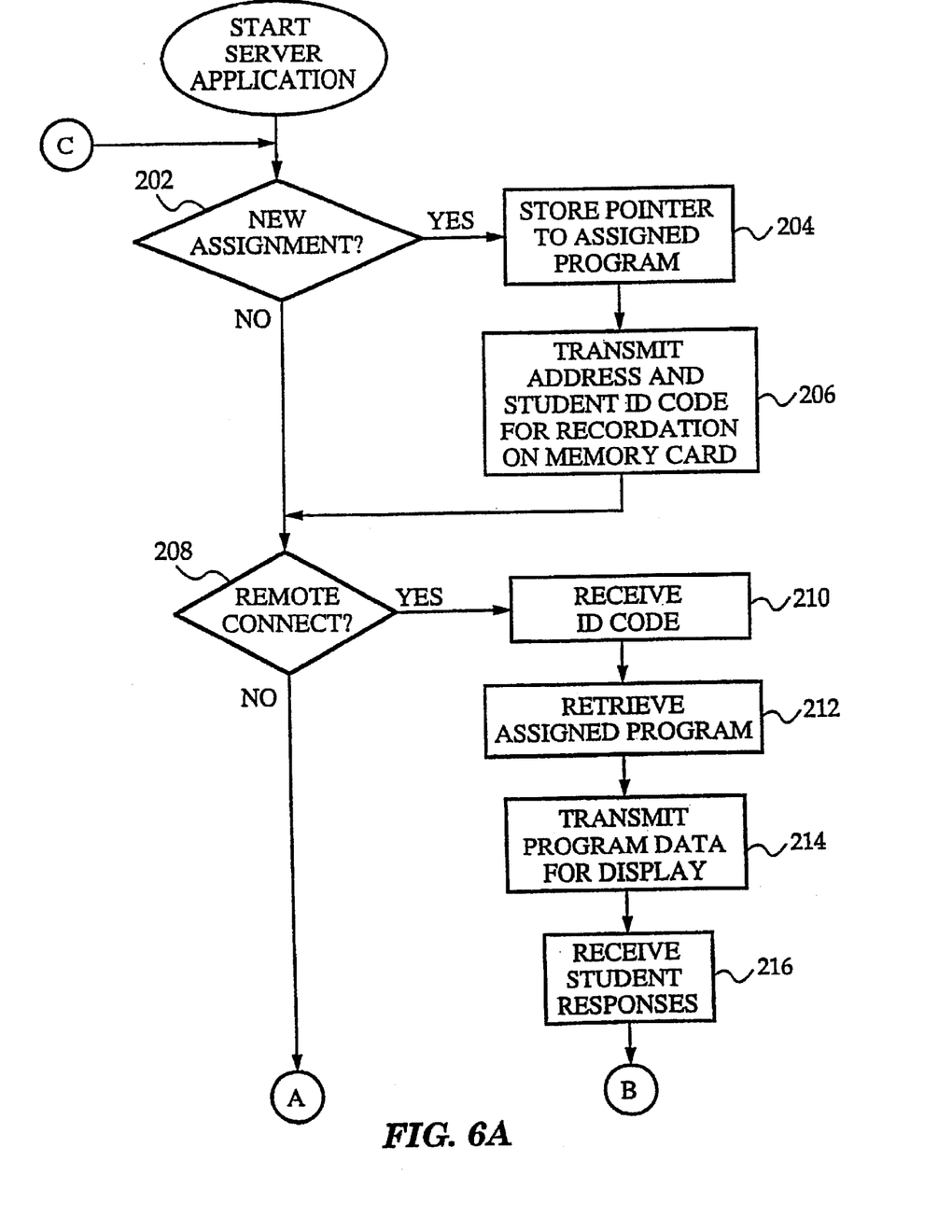
FIG. 6A is a flow chart illustrating the steps executed by the preferred embodiment of the present invention as shown in FIG. 1.
Figure 6B:
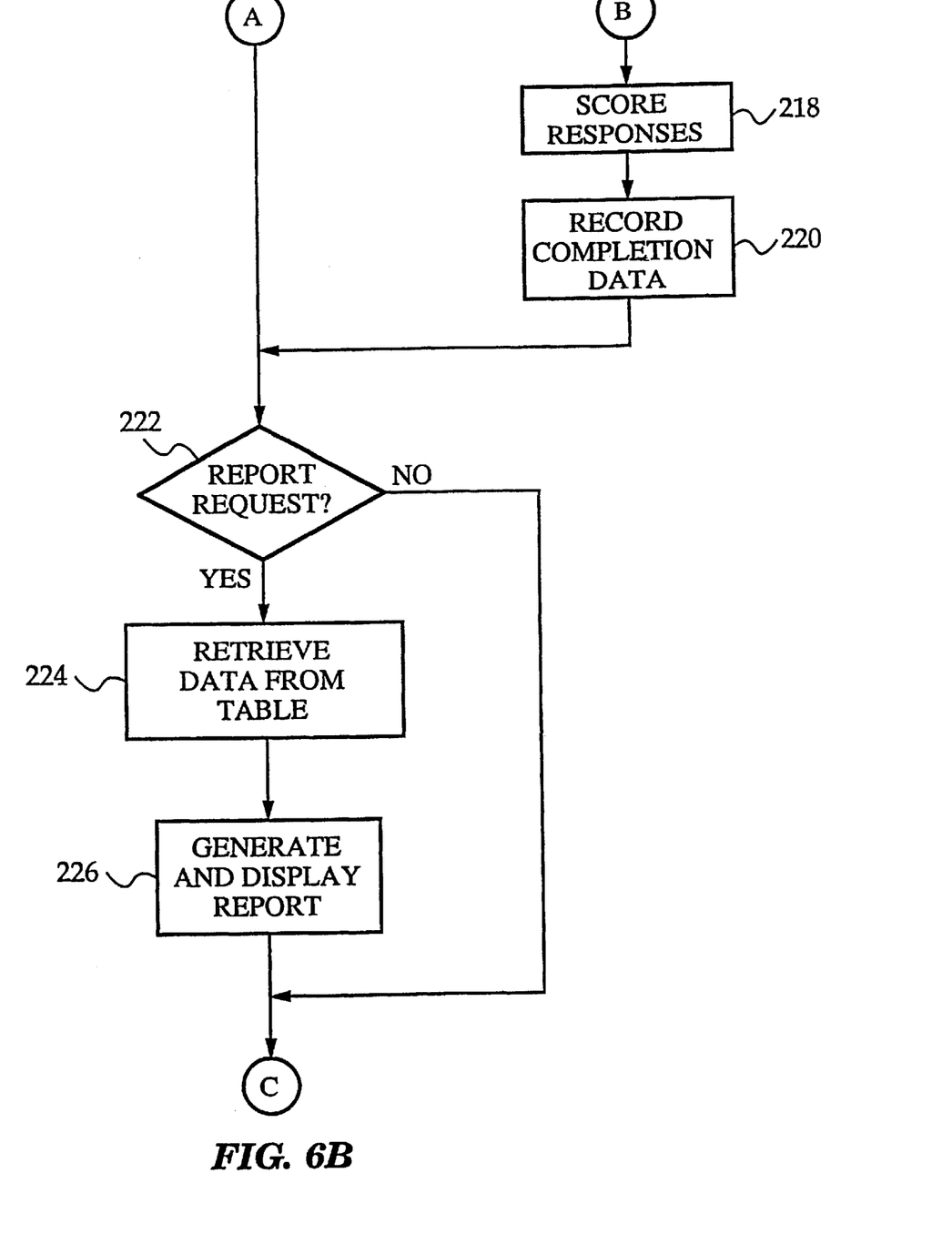
FIG. 6B is a continuation of the flow chart of FIG. 6A.

FIGS. 6A and 6B show a flowchart illustrating the steps carried out by the server 112 in the preferred embodiment of the present invention. In step 202, the file server 112 first preferably asks if the administrator would like to create a new assignment. Creating a new assignment preferably entails either adding a new patient to the patient table 146 or assigning a new educational program within the database 148 to a patient. If the administrator decides to create a new assignment, the information is preferably stored in the patient table 146, as shown in step 204. In step 206, the new assignment information consisting of the patient identification code 156 and the file server address 154 is also preferably recorded on the memory card 122 by the memory card writer 118, and then given to the patient. If the administrator does not need to create a new assignment, she preferably moves directly from step 202 to step 208.

After the patient returns home, he preferably places the memory card 122 into the memory card reader 126 which is preferably coupled to the multimedia processor 124. Preferably, the file server address 154 on the memory card 122 allows the multimedia processor 124 to locate and couple to the file server 112 in step 208. The patient identification code 156 is preferably then sent over in step 210. In step 212, the file server 112 then preferably finds the educational program within the database 148 assigned to patient in the patient table 146. The pointer in the database 144 then retrieves the educational program within the database 148. If the educational program is located in a remote database, it is sent through the file server 112 to the multimedia processor 124, as shown in step 214. Preferably, the memory means 160 of the multimedia processor 124 then interprets and translates the content of the educational program 148 into audiovisual signals to be shown on the display 128.

After the patient finishes watching the assigned educational program 148, a set of completion data comprising the time, date, and/or patient responses are preferably sent from the multimedia processor 124 to the file server 112 in step 216. Step 218 preferably scores the patient responses to determine a program score. Step 220 then preferably records the set of completion data in the patient table 146 of the file server 112.

If the administrator wishes to view the set of completion data belonging to a particular patient, she preferably requests a patient report, as shown in step 222. Step 222 preferably occurs after the patient has watched and responded to the educational program 148 in step 220, or at any time after step 208 if there is no remote connection. Preferably, the file server 122 retrieves the patient completion data from the patient table 146, step 224, and then shows it in the form of the report screen 152 on the display 116 in step 226. The report screen 152 as illustrated in FIG. 4 shows an exemplary display of the students, the assigned program, the set of completion data, and the program score.

Figure 7:
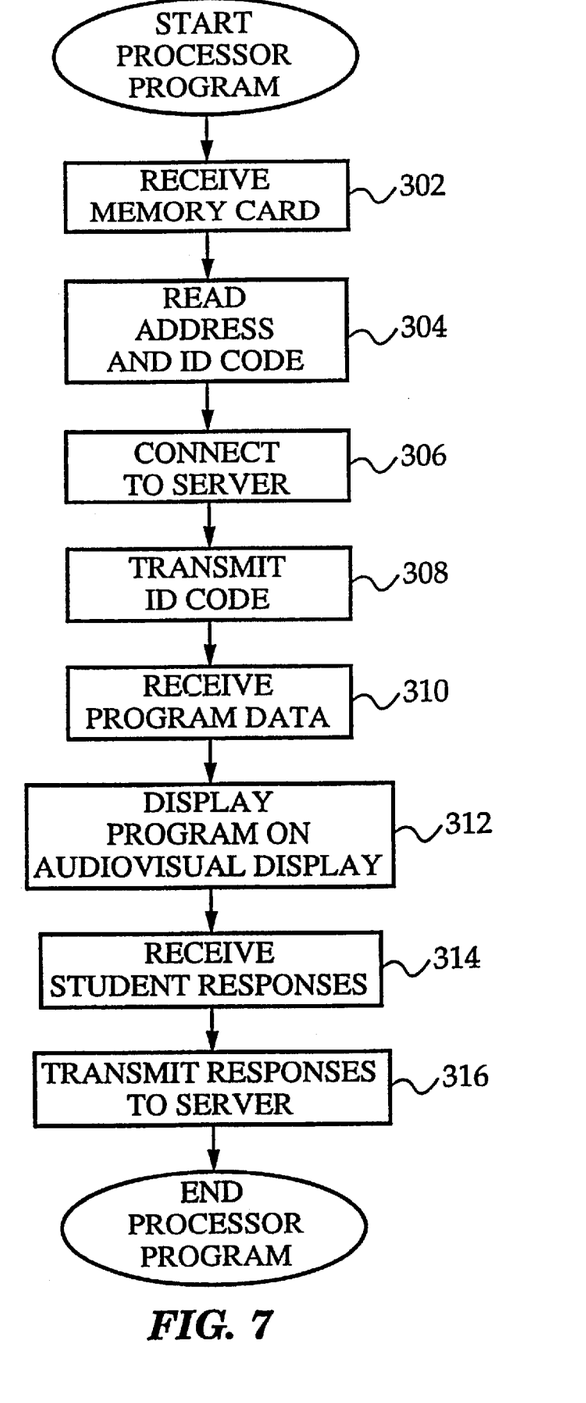
FIG. 7 is a flow chart illustrating the steps executed by the preferred embodiment of the present invention as shown in FIG. 1.

FIG. 7 is a flowchart outlining the steps involved in the processor program of multimedia processor 124 in the preferred embodiment of the present invention. The processor program may preferably be implemented by known software programs. The processor program preferably begins when the memory card 122 is placed in the memory card reader 126, as shown in step 302. Preferably, the memory card reader 126 scans the patient identification code 304 and the file server address 156 from the memory card 122 in step 304, and then sends the patient identification code 304 and the file server address 156 to the CPU 158. The file server address 156 preferably allows the CPU 158 to communicate with the file server 112 via the modem 164 in step 306. Subsequently, the patient identification code 154 is then preferably transmitted to the file server 112 in step 308. In step 310, the CPU 158 preferably receives the content of assigned educational program 148 via the modem 164. The content is preferably converted into audiovisual signals such that the content may be shown on the display 128 in step 312. The patient responses for the educational program within the database 148 is then preferably sent to the CPU 158 by the input device 134. Subsequently, the CPU 158 then preferably sends the program score and/or patient responses, along with other completion data, to the file server 112. The processor program of multimedia processor 124 then preferably ends.

The memory card reader 126 of the multimedia processor 124 preferably also has a writing function that is similar to the memory card writer 118 of the remote interface 114. This feature allows the program score to the educational program to be stored on memory card 122. The patient can then bring the memory card 122 to the healthcare provider or administrator for review. The memory card writer 118 of the remote interface 114 preferably also has reading capabilities. When the memory card 122 is inserted into the memory card writer/reader 118, the program scores are preferably downloaded into the remote interface 114. By bringing the memory card 122 to the healthcare provider, the patient is not required to transmit the patient responses over the communication link 140.

The present invention allows a healthcare provider or administrator to assign a remote educational program to a patient. The patient has the luxury of watching and responding to the program at the patient's own home and leisure. After the patient's response to the educational program, the data is then preferably transmitted to the file server and displayed for the administrator to view. Preferably, the administrator monitors whether or not the patient has watched the educational program, and can also evaluate the patient's responses to the program.

Appendix A shows one exemplary implementation of the present invention as it applies to working with a diabetes patient through MEDTV™ over the Internet. MEDTV™ is a trademark of Raya Systems, Inc. (Mountain View, Calif.).

Although the above description contains many specificities, these should not be construed as limitations on the scope of the present invention but merely details illustrating the presently preferred embodiment. Many other embodiments of the present invention are possible, as this invention can be used in any field where it is desirable to remotely educate an individual. For example, teachers may utilize the present invention to assign lessons to their students, and employers may utilize the present invention to provide additional job training for their employees.

An alternate embodiment of the present invention allows companies to promote their products. Preprogrammed memory cards can be placed with a company's products. For example, when the consumer buys a product, he also receives the preprogrammed memory card, which contains a code identifying the product and the address of the company's consumer-product file server. When the consumer places the memory card into the memory card reader of the multimedia processor, the multimedia processor automatically connects the consumer to the company's file server. The file server preferably contains a consumer-product table which stores a list of all the company's products with corresponding pointers to relevant educational programs or advertisements. As an example, a sunblock product would have a pointer to a short video on basic sun safety, as well as an advertisement for all sunblock products made by that company.

When the file server receives the product identification code from the multimedia processor, the file server preferably retrieves the relevant educational program or advertisement and sends the relevant portion back to the consumer's multimedia processor. The consumer may then watch the program or advertisement on the display.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

Specifically, it will be apparent to one of ordinary skill in the art that the device of the present invention could be implemented in several different ways and the apparatus disclosed above is only illustrative of the preferred embodiment of the invention and is in no way a limitation. For example, it would be within the scope of the present invention to substitute various output devices in place of the displays and to substitute a floppy disk drive and a floppy diskette for the memory card reader/writer and the memory card, respectively. Further, it would be within the scope of the present invention to substitute the database for a plurality of databases linked via the Internet.

What is claimed is:

1. A remote education system comprising:
   a. a database for storing an educational program;
   b. a file server coupled to the database;
   c. a remote interface coupled to the file server for assigning the educational program to an individual thereby forming an assigned program, wherein the file server includes a memory means for storing an identification code of the individual and a pointer directed to the assigned program;
   d. a memory card for storing the identification code and an electronic address of the file server;
   e. a display unit for displaying the assigned program;
   f. a multimedia processor networked to the file server and coupled to the display unit; and
   g. a card reader coupled to the multimedia processor for receiving the memory card and for reading the identification code and the electronic address stored thereon, wherein the multimedia processor is programmed to establish a communication link to the file server, transmit the identification code to the file server, and automatically display the assigned program on the display unit, and wherein the file server is programmed to record data indicating completion of the assigned program by the individual.

2. The system according to claim 1, further comprising a memory card writer coupled to the remoter interface for recording the identification code and the electronic address onto the memory card.

3. The system according to claim 1, wherein the multimedia processor establishes the communication link to the file server upon insertion of the memory card into the card reader.

4. The system according to claim 1, wherein the data indicating completion of the assigned program comprises a date and a time of completion.

5. The system according to claim 1, wherein the data indicating completion of the assigned program comprises a program score, which is produced by evaluating a response by the individual to the assigned program, wherein the response is transmitted from the multimedia processor to the file server.

6. The system according to claim 1, wherein the memory card further comprising a circuit for storing the identification code and the electronic address.

7. The system according to claim 1, wherein the data indicating completion of the assigned program is reported on the remote interface.

8. The system according to claim 1, wherein the assigned program is used to educate the individual in a healthcare program.

9. The system according to claim 1, wherein the memory card further comprising a magnetic strip for storing the identification code and the electronic address.

10. The system according to claim 1, wherein the file server comprises a web server, the remote interface comprises a web page for assigning the educational program to the individual, and the communication link comprises a computer network.

11. The system according to claim 10, wherein the data indicating completion of the assigned program further comprising a start date and a start time the individual logged on to the assigned program and a stop date and a stop time the individual logged off of the assigned program.

12. The system according to claim 10, wherein the data indicating completion of the assigned program further comprising a program score, which is produced by evaluating a response of the individual to the assigned program, wherein the response is transmitted from the multimedia processor to the file server via the computer network.

13. The system according to claim 10, wherein the data indicating completion of the assigned program is reported on the web page of the remote interface.

14. A method for educating an individual, the method comprising the following steps:
   a. providing the individual with a memory card reader, a display unit, and a multimedia processor wherein the multimedia processor is coupled to the card reader and the display unit;
   b. storing an educational program on a database wherein the educational program is accessible to the individual through a file server;
   c. assigning the educational program to the individual thereby forming an assigned program by storing both an identification code of the individual and a pointer directed to the assigned program in the file server;
   d. recording on a memory card an electronic address of the file server and the identification code;
   e. inserting the memory card into the card reader;
   f. automatically establishing a communication link between the multimedia processor and the file server upon insertion of the memory card into the card reader;
   g. transmitting the identification code to the file server;

h. automatically retrieving the assigned program from the database;

i. automatically displaying the assigned program on the display unit; and j. recording, in the file server, data indicating completion of the assigned program by the individual.

15. The method according to claim 14, wherein the step of recording the data indicating completion of the assigned program further comprising: storing in the file server a date and a time that the individual completed the assigned program.

16. The method according to claim 14, wherein the step of recording the data indicating completion of the assigned program further comprising:

a. receiving an answer into the multimedia processor wherein the answer is made by the individual in response to the assigned program;

b. transmitting the answer from the multimedia processor to the file server;

c. evaluating the answer in the file server to generate a program score; and d. storing the program score in the file server.

17. The method according to claim 14, further comprising: reporting on a remote interface the data indicating completion of the assigned program.

18. The method according to claim 14, wherein the memory card further comprising a magnetic strip for storing the identification code and the electronic address.

19. The method according to claim 14, wherein the memory card further comprising: a circuit for storing the identification code and the electronic address.

20. The method according to claim 14, wherein the assigned program is used to educate the individual in a healthcare program.

21. The method according to claim 14, wherein the file server comprises a web server, a remote interface comprises a web page for assigning the assigned program to the individual, and the communication link comprises a computer network.

22. The method according to claim 21, wherein the step of recording data indicating completion of the assigned program further comprising: storing in the file server a start date and a start time that the individual logged on to the assigned program, a stop date and a stop time that the individual logged off of the assigned program.

23. The method according to claim 21, wherein the step of recording data indicating completion of the assigned program further comprising:

a. receiving in the multimedia processor the answer made by the individual in response to the assigned program;

b. transmitting the answer from the multimedia processor to the file server via the computer network;

c. evaluating the answer in the file server to generate a program score; and d. storing the program score in the file server.

24. The method according to claim 21, further comprising: reporting on the web page of the remote interface the data indicating completion of the assigned program.

* * * * *

UNITED STATES PATENT AND TRADEMARK OFFICE
CERTIFICATE OF CORRECTION

PATENT NO.    : 6,330,426 B2
DATED         : December 11, 2001
INVENTOR(S)   : Brown et al.

It is certified that error appears in the above-identified patent and that said Letters Patent is hereby corrected as shown below:

<u>Title page,</u>
Item [63], Related U.S. Application Data, delete "No. 5,601,435, which is a continuation-in-part of application No. 08/857,187, filed on May 15, 1997, now Pat. No. 5,918,603, which is a continuation-in-part of application No. 08/247,716, filed on May 23, 1994, now Pat. No., 5,678,751"
and insert instead:
-- No. 5,601,435, and a continuation-in-part of application No. 08/958,786, filed on October 29, 1997, now Pat. No. 5,913,603, which is a continuation-in-part of application No. 08/857,187, filed on May 15, 1997, now Pat. No. 5,918,603 which is a divisional of application No. 08/247,716, filed on May 23, 1994, now Pat. No. 5,678,571 --

<u>Column 2,</u>
Line 11, delete "show" and insert instead -- shows --

<u>Column 5,</u>
Line 26, following the word "used" insert -- to --
Line 39, delete "28" and insert instead -- 128 --
Line 57, following the word "to" insert -- an --

<u>Column 6,</u>
Line 6, delete "button"
Line 50, delete "126" and insert instead -- 126, --
Line 56, delete "40" and insert instead -- 140 --

<u>Column 7,</u>
Line 37, preceding the word "patient" insert -- a --

UNITED STATES PATENT AND TRADEMARK OFFICE
CERTIFICATE OF CORRECTION

PATENT NO.   : 6,330,426 B2
DATED        : December 11, 2001
INVENTOR(S)  : Brown et al.

It is certified that error appears in the above-identified patent and that said Letters Patent is hereby corrected as shown below:

<u>Column 9,</u>
Line 67, delete "remoter" and insert instead -- remote --

Signed and Sealed this

Second Day of December, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,330,426 B2
DATED : December 11, 2001
INVENTOR(S) : Brown et al.

It is certified that error appears in the above-identified patent and that said Letters Patent is hereby corrected as shown below:

Title page,
Item [63], Related U.S. Application Data, should read
-- This application is a continuation-in-part of the application Ser. No. 08/953,883 filed on Oct. 20, 1997, now abandoned which in turn is a continuation-in-part of application Ser. No. 08/757,129 filed on Dec. 3, 1996, which is now U.S. Pat. No.6,144,837 issued on Nov. 7, 2000, which in turn is a continuation of patent application Ser. No. 08/334,643 filed on Nov. 4, 1994, which is now U.S. Pat. No. 5,601,435 and a continuation-in-part of application Ser. No. 08/958,786, which is now U.S. Pat. No. 5,913,310, issued on Jun. 22, 1999, which is a continuation-in-part of application Ser. No. 08/857,187, filed May 15, 1997, now U.S. Pat. No. 5,918,603 which is a continuation of application Ser. No. 08,247,716, filed May 23, 1994, now U.S. Pat. No. 5,678,571, issued on Oct. 21, 1997. --

Signed and Sealed this

Twenty-ninth Day of June, 2004

JON W. DUDAS
*Acting Director of the United States Patent and Trademark Office*